US00PP09035P

United States Patent [19]

Desclaux

[11] Patent Number: Plant 9,035

[45] Date of Patent: Jan. 3, 1995

[54] CARNATION NAMED KRISTINA

[75] Inventor: Jean-Louis Desclaux, Angers, France

[73] Assignee: Laboratorie Physilogie Vegetale, Le Pradet, France

[21] Appl. No.: 189,444

[22] Filed: Jan. 31, 1994

[51] Int. Cl.[6] ..... A01H 5/00

[52] U.S. Cl. ..... Plt./70.1

[58] Field of Search ..... Plt. 71.1, 70.1

[56] References Cited

PUBLICATIONS

Huxley, A. et al., "Dianthus" *The New Royal Horticultural Society Dictionary of Gardening* vol. 2, 1992, Stocton Press, N.Y., pp. 50–56.

*Primary Examiner*—James R. Feyrer

*Attorney, Agent, or Firm*—Tilton, Fallon, Lungmus & Chestnut

[57] ABSTRACT

A new standard carnation cultivar particularly distinguished by light pink colored flower petals having violet spots, which may occasionally be elongated, wherein each petal is bordered with a slightly serrated margin of violet. These flowers are medium in size, borne singly on long, strong stems and bloom profusely during the recurrent blooming seasons of Spring and Fall. This plant has a vigorous upright growth habit and abundant foliage.

1 Drawing Sheet

BACKGROUND OF THE NEW PLANT

This carnation cultivar originated as a hybrid seedling produced in a nursery at San Remo, Italy by my crossing of two plants, hereinafter identified, selected from a field of various carnation varieties maintained at my nursery for breeding purposes. This particular seedling was selected from those produced by said hybridization because of the unusual flower coloration on a plant having moderately abundant foliage, favorable growth characteristics and tolerance to *Fusarium oxysporum*. After isolation of the selected plant, vegetative propagation was made by cuttings or by in vitro culture. The said propagation was made at our laboratory located in Le Pradet (France). Under my direction, propagation was done by means of cuttings. The initial success of the propagation was continued through several successive generations which proved that the new variety retained all of the distinguished characteristics hold true from generation to generation and appear to be firmly fixed.

DESCRIPTION OF THE DRAWING

This new carnation cultivar is illustrated by the accompanying photographic drawing which, in full color, shows the distinguishing color characteristics and flower form of this plant, the color rendition being as nearly true as it is reasonably possible to obtain by conventional photographic procedures.

DESCRIPTION OF THE NEW PLANT

The following is a detailed description of our new carnation plant with the color designations according to The R.H.S. Color Chart of The Royal Horticultural Society of London, England.

THE PLANT

Origin: Seedling.

Parentage:

*Seed parent.*—Plant 208 (Unpatented). Plant 208 is a standard carnation having white petals with slightly serrated margins of violet. The stem of plant 208 is thick and straight and has a length of 64.3 cm at the tenth node. Plant 208 is not commercially available. Pollen Plant: Plant 330 (Unpatented). Plant 330 is a standard carnation having light pink petals with a serrated margins. The stem of plant 330 is not very thick, but is straight. The length of the stem of 330 is 68.5 cm at the tenth node. Plant 330 is not commercially available. These parent plants are so identified in my business records of the present cultivar maintained at the office of the San Remo, Italy, nursery and the production of the aforementioned hybrid and the selected seedling are also there recorded.

Classification:

*Botanic.*—*Dianthus caryophyllus.*

*Commercial.*—Standard carnation.

Form: Erect bush having at least four stems emitted near the ground.

Height: Approximately 105.8 cm in average at 8 months.

Internode length: 7.88 cm between the 4th and 5th node.

Main stem length: Approximately 64.3 cm at the tenth node.

Cane length: Less than 15 cm because of pinching.

Strength: Strong.

Branching character: This plant is moderately branched.

Growth: Vigorous and upright.

Foliage:

*Quantity.*—Medium.

*Number of leaves.*—More than 120.

*Size of leaf.*—Approximately 12.5 cm×1 cm at the 7th node.

*Leaf shape.*—Fusiform.

*Margin type.*—Smooth, typical of the genus.

*Texture.*—Leathery.

*Color.*—Upper side — RHS 137-A. Under side — RHS 137-A.

Reflexing of the leaves: The leaves bend slightly downward at an angle of 35 degrees with the stem.

Surface bloom: The leaves and stem contain a very thin layer of waxy surface bloom. This surface bloom is only microns in thickness. If the waxy layer is removed from the leaves of the stem, the color of the leaves or the stem becomes a darker green. The leaf color beneath the surface bloom is RHS 137-A.

THE BUD

Size:
- *Diameter.*—Averages about 2.1 cm.
- *Length.*—Averages about 3.0 cm.
- *Shape.*—Ovoid.

Rate of opening: Normal for carnations.

Color of petals:
- *When sepals first divide.*—RHS 11-D and RHS 71-D.
- *When petals begin to unfurl.*—RHS 27-D and RHS 71-D.

Sepals:
- *Number.*—Approximately 5–7.
- *Shape.*—The sepals are hooded over the bud before dividing and stand up as the flower petals unfurl. The sepals are joined together at the lower part and sharp pointed at the extremity.
- *Color.*—Inside — RHS 149-D. Outside — RHS 143-D.

Striae: Longitudinal striae.

Calyx:
- *Shape.*—Campanulate.
- *Size.*—Long.
- *Splitting.*—The calyx does not split.
- *Aspect.*—Glandular.

Flower stem:
- *Length.*—About 64.3 cm in average.
- *Character.*—Rigid and erect.
- *Color.*—RHS 137-A.

THE FLOWER

Blooming habit: Recurrent and profuse during the mid-season of Spring and Fall.

Size of bloom: Medium.
- *Diameter.*—About 8.4 cm in average.
- *Depth.*—About 3.4 cm in average.

Borne: Singly.

Shape:
- *When the bloom first opens.*—High centered.
- *When bloom matures.*—High centered.

Petalage:
- *Number of petals.*—Averages about 67.
- *Arrangement.*—Imbricated.
- *Form.*—Fan-shaped with a waved outer margin.
- *Texture.*—Leathery.
- *Margin type.*—Slightly serrated.
- *Appearance.*—Satiny.
- *Color.*—Outer petal: The body has the color RHS 56-D. The border has the color RHS 71-A. Also, the spots on the body have the color — RHS 71-A. Base: RHS 145-B. Reverse side: The body has the color RHS 56-D. The border has the color RHS 71-A. Also, the spots on the body have the color — RHS 71-A. Inside petal: About the same as the outer petals. Base: RHS 145-B. Spots: As indicated above, the color of the spots on the petals in RHS 71-A. The size of the spots on the petals does not change with the season. Additionally, the spots are randomly distributed on the petals.

Discoloration after full bloom: The color of the body becomes RHS 56-C and border and spots have the color RHS 71-C.

Persistence: The petals hang on and dry for more than 20 days.

Fragrance: A light fragrance is perceptible. The fragrance is typical of the genus *Dianthus caryophyllus.*

Lasting quality:
- *As a cut flower.*—At least 10 days with vase keeping.

Is the bloom affected by wet or hot weather: No.

Disease resistance: Tolerant to *Fusarium oxysporum.*

THE REPRODUCTIVE ORGANS

Stamens:
- *Number.*—3 to 8.
- *Arrangement.*—Around the ovary.
- *Anthers.*—Size: About 3 mm. Color: Cream.
- *Filaments.*—Length: About 1.2 cm in average. Color: Cream.
- *Pistils.*—Number: About 3 to 4.
- *Styles.*—Length: About 3.1 cm in average. Color: Cream.
- *Stigmas.*—Color: Cream with traces of violet.

Character of ovaries: The ovary is slightly ribbed.

This new variety most closely resembles Digimas. Digimas is unpatented but commercially available. Kristina is particularly distinguished by its small flower, abundant flower spots and more intense color.

Fertile: Yes.

Fruit: Yes.

I claim:

1. A new and distinctive carnation cultivar substantially as herein shown as described, characterized by its light pink flowers having violet spots, which may occasionally be elongated, borne singly on long, strong stems, the flowers being characterized by petals which have a slightly serrated margins violet in color.

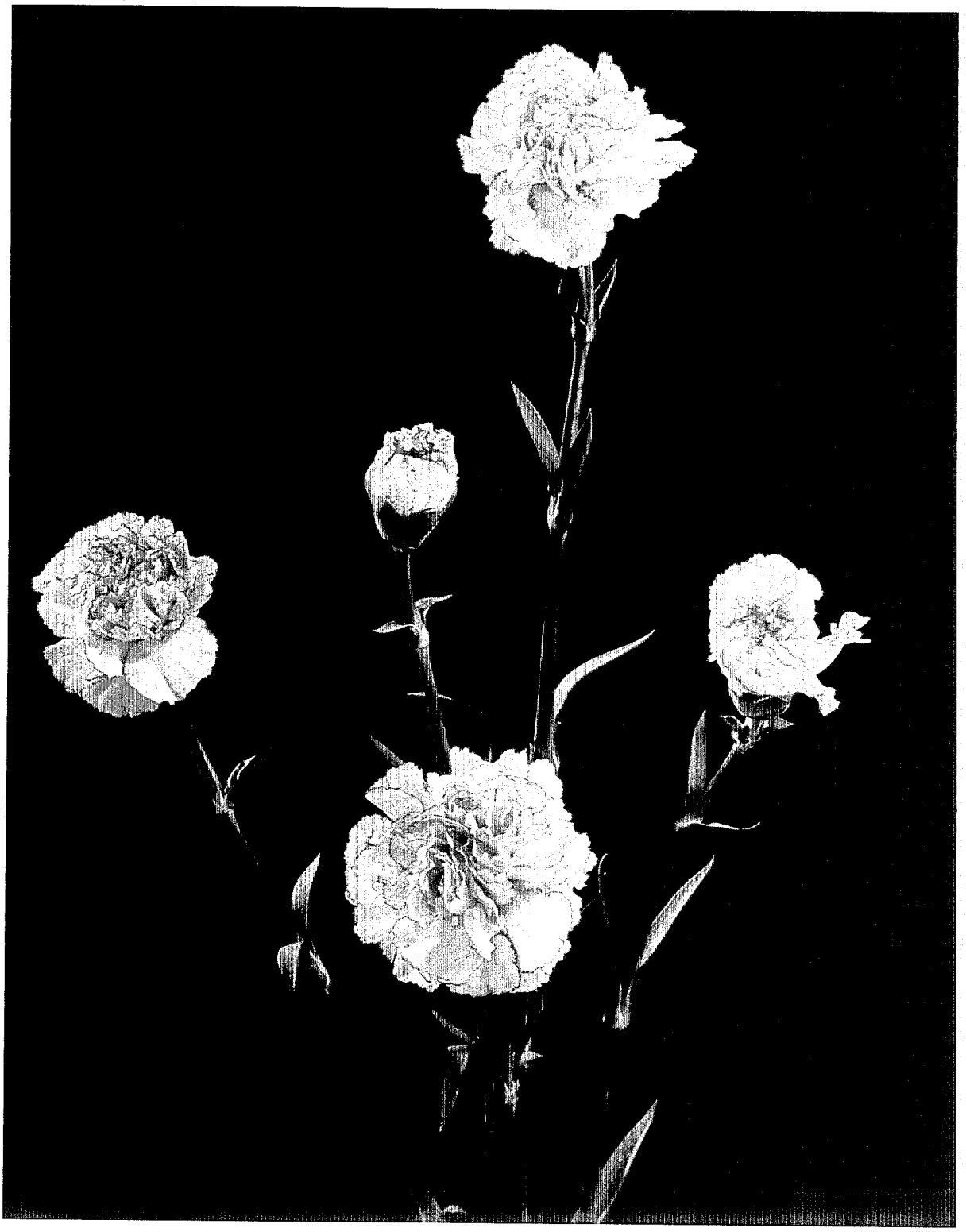

* * * * *